(12) United States Patent
Taylor

(10) Patent No.: US 7,846,186 B2
(45) Date of Patent: Dec. 7, 2010

(54) EQUIPMENT FOR SURGICAL TREATMENT OF TWO VERTEBRAE

(75) Inventor: Jean Taylor, Cannes (FR)

(73) Assignee: Kyphon SÀRL, Neuchâtel (CH)

( * ) Notice: Subject to any disclaimer, the term of this patent is extended or adjusted under 35 U.S.C. 154(b) by 382 days.

(21) Appl. No.: 11/994,195

(22) PCT Filed: Jun. 20, 2006

(86) PCT No.: PCT/IB2006/001639

§ 371 (c)(1),
(2), (4) Date: Dec. 28, 2007

(87) PCT Pub. No.: WO2007/000634

PCT Pub. Date: Jan. 4, 2007

(65) Prior Publication Data

US 2008/0215094 A1    Sep. 4, 2008

Related U.S. Application Data

(60) Provisional application No. 60/694,672, filed on Jun. 29, 2005.

(30) Foreign Application Priority Data

Jun. 28, 2005    (FR) .................................. 05 06541

(51) Int. Cl.
*A61B 17/70* (2006.01)
(52) U.S. Cl. .................. 606/249; 606/248; 606/246
(58) Field of Classification Search .................. 606/61, 606/69, 246–249, 279; 623/17.11–17.16
See application file for complete search history.

(56) References Cited

U.S. PATENT DOCUMENTS

| 624,969 | A | 5/1899 | Peterson |
| 1,153,797 | A | 9/1915 | Kegreisz |
| 1,516,347 | A | 11/1924 | Pataky |
| 2,077,804 | A | 4/1937 | Morrison |
| 2,299,308 | A | 10/1942 | Creighton |

(Continued)

FOREIGN PATENT DOCUMENTS

DE    2821678 A1    11/1979

(Continued)

OTHER PUBLICATIONS

International Search Report of PCT/IB2006/001639 filed Jun. 20, 2006, date of mailing Oct. 19, 2006.

(Continued)

*Primary Examiner*—Eduardo C Robert
*Assistant Examiner*—Christina Negrelli
(74) *Attorney, Agent, or Firm*—Coats and Bennett, P.L.L.C.

(57) ABSTRACT

The equipment (1) includes:
  bone anchor elements (2) that will be anchored in a first of the two treated vertebrae (100), and
  two rigid walls (3) that can be connected to the bone anchor elements (2), that will be arranged on each side of the spinous process (101) of the second treated vertebra (100) with no connection to it and sized to extend over at least the height of the spinous process (101), these walls (3) thus being capable of limiting pivot movements of this second vertebra (100) about an axis approximately perpendicular to the intervertebral disk.

12 Claims, 3 Drawing Sheets

U.S. PATENT DOCUMENTS

| | | |
|---|---|---|
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,401,112 A | 8/1983 | Rezaian |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,659 A | 5/1995 | Lee et al. |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,458,641 A | 10/1995 | Ramirez Jimenez |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,447,513 B1 | 9/2002 | Griggs |
| 6,451,019 B1 | 9/2002 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |

| | | |
|---|---|---|
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,611,316 B2 | 11/2009 | Panasik et al. |
| 2002/0143331 A1 | 10/2002 | Zucherman et al. |
| 2003/0040746 A1 | 2/2003 | Mitchell et al. |
| 2003/0065330 A1 | 4/2003 | Zucherman et al. |
| 2003/0153915 A1 | 8/2003 | Nekozuka et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1* | 4/2006 | Borgstrom et al. ............ 606/61 |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0293662 A1 | 12/2006 | Boyer, II et al. |
| 2006/0293663 A1 | 12/2006 | Walkenhorst et al. |
| 2007/0032790 A1 | 2/2007 | Aschmann et al. |
| 2007/0043362 A1 | 2/2007 | Malandain et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0270834 A1 | 11/2007 | Bruneau et al. |
| 2007/0276369 A1 | 11/2007 | Allard et al. |
| 2007/0276493 A1 | 11/2007 | Malandain et al. |
| 2007/0282443 A1 | 12/2007 | Globerman et al. |
| 2008/0021457 A1 | 1/2008 | Anderson et al. |
| 2008/0058934 A1 | 3/2008 | Malandain et al. |
| 2008/0161818 A1 | 7/2008 | Kloss et al. |
| 2008/0183211 A1 | 7/2008 | Lamborne et al. |
| 2008/0183218 A1 | 7/2008 | Mueller et al. |
| 2008/0221685 A9 | 9/2008 | Altarac et al. |
| 2008/0262617 A1 | 10/2008 | Froehlich et al. |
| 2009/0234389 A1 | 9/2009 | Chuang et al. |
| 2009/0270918 A1 | 10/2009 | Attia et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 0 928 603 A1 | 7/1999 |
| EP | 1004276 A1 | 5/2000 |
| EP | 1 138 268 A1 | 10/2001 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| FR | 2884135 A1 | 4/2005 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | 03/103519 A2 | 12/2003 |
| WO | WO 2004/047689 A1 | 6/2004 |

| WO | WO 2004/047691 A1 | 6/2004 |
| WO | WO 2004/084768 A2 | 10/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2006/110578 A2 | 10/2006 |
| WO | WO 2007/034516 A1 | 3/2007 |
| WO | WO 2007/052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur, Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèese," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopedique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Wittenberg et al., "Flexibility and Distraction after Monosegmental and Bisegmental Lumbrosacral Fixation with Angular Stable Fixators," SPINE, 1995, pp. 1227-1232, vol. 20, No. 11.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

\* cited by examiner

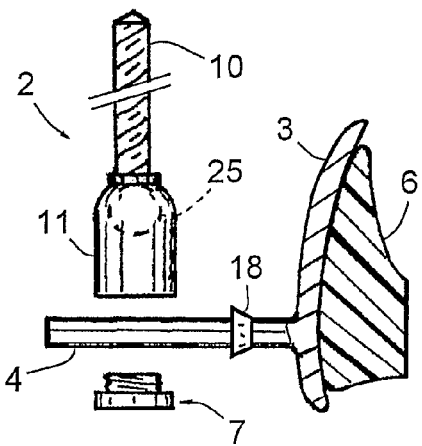 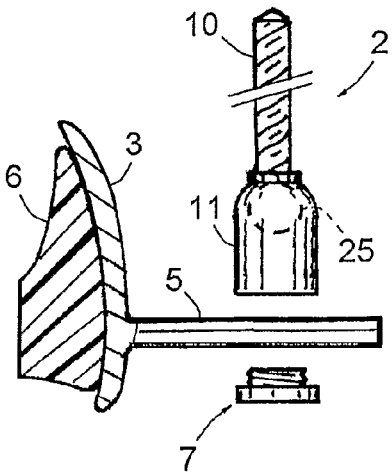
FIG. 8
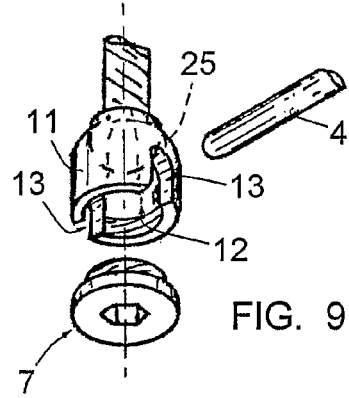 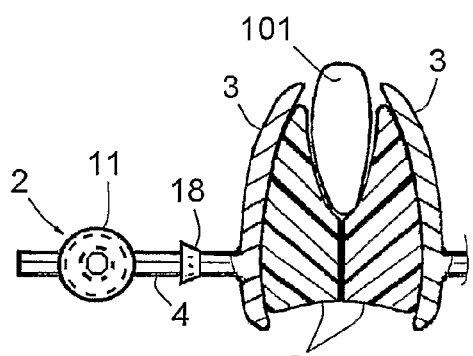
FIG. 9  FIG. 10
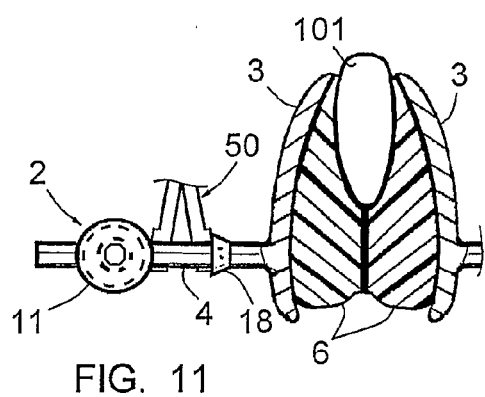
FIG. 11
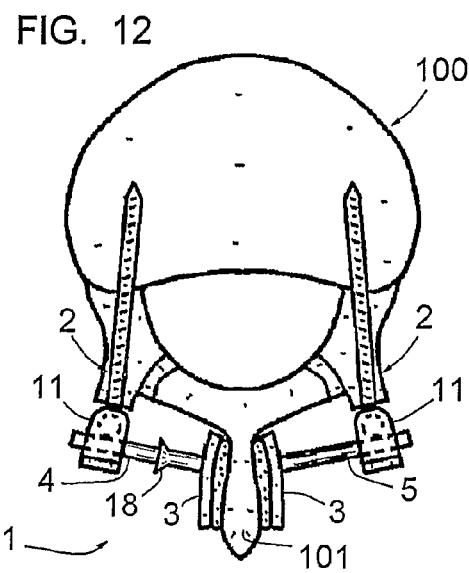 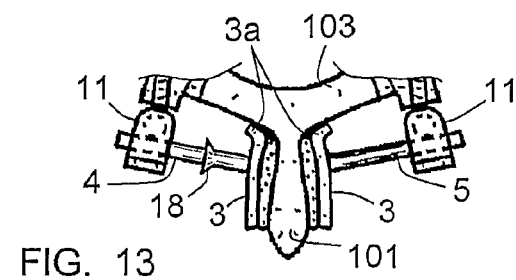
FIG. 12  FIG. 13

EQUIPMENT FOR SURGICAL TREATMENT OF TWO VERTEBRAE

This invention relates to equipment for the surgical treatment of two vertebrae.

It is known that movements of vertebrae about the axis of the spinal column, in other words in torsion about the spinal column, are known to cause serious pathologies. Due to its structure, the intervertebral disk is particularly vulnerable to this type of torsion stresses which become irreversible beyond a certain amplitude. This weakness is obvious, particularly within the framework of disk facet degeneration phenomena.

These pathologies may apply to two vertebrae only, particularly the fourth and fifth lumbar vertebrae. A degeneration of retention elements, particularly ligaments and/or posterior joint bone masses, leads to a number of disorders including a disorder known under the term "rotational spondylolisthesis".

The following therapeutic solutions are available at the present time to deal with such a rotational instability:

1—cauterisation of disk fibres that generate pain, or nerve ramifications of the posterior joints by heat or radio frequencies;

2—osteosynthesis systems by pedicle screws and junction rods;

3—placement of an implant between vertebral bodies;

4—placement of rigid or shock absorbing inter-process prostheses;

5—posterior joint prostheses.

The disadvantage of these therapeutic solutions is that they do not usually genuinely satisfy the double requirement for the treatment of pain and respect of controlled amplitude movements, which cannot be dissociated. They also have the specific disadvantages mentioned below:

1—cauterisation: this technique is not reliable. Percutaneous identification is very uncertain, and all that is supposed to be taken into account is perception of pain.

2—osteosynthesis systems: this type of set up cannot give good biomechanical control of torsions, and screws have to be placed in the pedicles of the upper vertebra (for example L4) to neutralise two vertebrae (for example L4-L5); but these pedicles belong to the superjacent functional unit, that is thus damaged or at least compromised.

3—implant between vertebral bodies: placement of such an implant cannot be stable in torsion; it is counter-indicated with arthropathy of the facets and cannot prevent degeneration phenomena of posterior joint bone masses, but may even accelerate them. These techniques are also affected by a non-negligible number of complications.

4—inter-process prostheses: doubtful biomechanical efficiency, regarding torsion movements that are badly retained.

5—posterior joint prostheses: still at a design stage, particularly because it appears very difficult to take account of the complex parameters that they induce in terms of material definitions, implantation technique and particularly durability.

This invention is designed to correct all the disadvantages of existing techniques.

Document US 2003/040746 describes a rigid element 58 bearing either only on the spinous process of the two vertebrae (see FIGS. 1, 9), or at the spinous process of two vertebrae and the sacrum or vertebral pedicles of the superjacent vertebra (see FIG. 22). It is considered that systems according to this document do not overcome disadvantages of existing techniques.

Therefore the main objective of this invention is to provide vertebral contention equipment capable of treating two vertebrae, particularly lumbar vertebrae, in order to enable the possibility of an indolent movement.

Consequently, this equipment comprises:

bone anchor means that will be anchored in a first of the two treated vertebrae, and two rigid walls that can be connected to the bone anchor means, that will be arranged on each side of the spinous process of the second treated vertebra with no connection to it and sized to extend over at least the height of the spinous process, these walls thus being capable of limiting pivot movements of this second vertebra about an axis approximately perpendicular to the intervertebral disk.

The equipment according to the invention thus comprises two rigid walls that will be arranged on each side of the spinous process and the lamina of one of the treated vertebrae, particularly the superjacent vertebra, and will maintain contention for lateral and torsional movements of this vertebra, and is implanted near only one other vertebra, preferably the subjacent vertebra.

Consequently, this equipment is capable of conserving said lateral and torsional movements while limiting them so that they remain within physiological amplitudes, by replacing or assisting the defective natural retention elements, particularly ligaments and/or posterior joint bone masses, and disk annulus elements. Furthermore, this material does not limit other joint movements between the two vertebrae concerned.

Excessive movements beyond the physiological amplitude, that are the source of pain and joint degeneration, are eliminated, and the natural torsional movement of the vertebrae is respected, and also controlled.

Furthermore, the equipment according to the invention may be qualified as being a "posterior shock absorbing disk facet controlling prosthesis", since it is capable of firstly protecting the front and back of the disk, and secondly reducing impaction and trapping phenomena between joint facets in contact so as to control their clearance.

The indications of the equipment according to the invention are particularly:

cases of facet arthropathies, regardless of which they are primitive or consecutive to disk degeneration, or even a diskectomy;

rotational spondylolisthesis;

prevention of degeneration syndromes occurring between vertebrae located above vertebrae on which arthrodesis has been done;

treatment of recurrent disk post-arthroplasty lumbago.

Preferably, said walls are sized so as to extend forwards after implantation, as far as the junction of the spinous process of second said vertebra with the lamina of the posterior arc.

Therefore, after implantation said walls are located at the base of said spinous process, such that conservation of movement according to the equipment according to the invention respects the torsion axis of the vertebra.

The equipment preferably comprises elastic or viscoelastic means for damping lateral and torsional movements of said second vertebra. "Viscoelastic" means material with a stiffness which varies with the state of compression of this material, this material tending to become increasingly rigid as it is compressed. Putting the elastic or viscoelastic means into compression, when the walls are moved towards the spinous process, prestresses said means, providing it with this programmed control characteristic.

These elastic or viscoelastic means are preferably located between said walls and said spinous process. In other words, they clad the median face of the walls.

Advantageously in this case, said walls extend beyond the spinous process of said second vertebra towards the spinous process of said first vertebra, and the elastic or viscoelastic means are shaped so that they are present between the spinous process of said second vertebra and the spinous process of said first vertebra.

Thus, in addition to control of said lateral movements, the equipment according to the invention dampens the bending/extension movement of the vertebrae and restores good alignment of the facets, particularly by raising the posterior arc of said second vertebra, leading to control over the joint clearance of the facets thus raised.

Said walls preferably surround the elastic or viscoelastic means to assure longitudinal support of these elastic or viscoelastic means. In particular, they may be in the form of shells with concave shapes on their sides that will face the spinous process that is under contention by the shells.

The elastic or viscoelastic means may be made in a single piece or they may be made of two symmetric parts, being positioned on each side of the spinous process of said second vertebra.

Making these elastic or viscoelastic means in two symmetric parts has the advantage of conserving the supraspinous ligament. Furthermore, each part can be put into compression independently.

The anchor means are preferably polyaxial pedicle screws, in other words including articulations between their parts that will be anchored in the vertebral pedicles and their parts that will be connected to said walls.

These walls may thus be positioned independently of the position of said parts that will be anchored in the vertebral pedicles.

The two walls may or may not be connected to each other. If they are connected, the elastic or viscoelastic element may be in a single-piece and it may click inside the housing formed by the two walls.

The invention will be clearly understood and other characteristics and advantages of the invention will become clear with reference to the appended diagrammatic drawing showing two possible embodiments of the equipment that it concerns as non-limitative examples.

FIG. 8 is an elevation and partial sectional view of this equipment according to the second embodiment;

FIG. 9 is an exploded partial perspective view;

FIGS. 10 and 11 are partial views of the equipment similar to FIG. 8, before and after the elastic elements included in it are put into compression, respectively;

FIG. 12 is a view after implantation on a vertebra along the apico-caudal axis.

FIG. 13 is a view similar to FIG. 12, of one variant.

For simplification reasons, parts or elements of one embodiment identical to or similar to parts or elements of another embodiment will be identified with the same numeric references and will not be described further.

Figure 1:
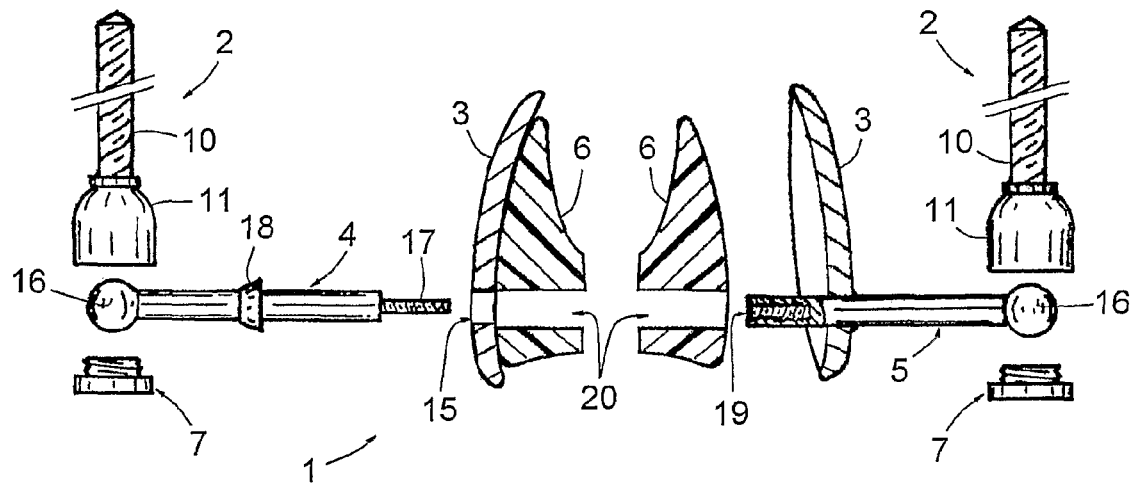
FIG. 1 is a partial sectional elevation of said equipment according to a first embodiment.

FIG. 1 shows a surgical treatment equipment 1 of two vertebrae that includes two pedicle screws 2, two shells 3, two connecting rods 4, 5 of the shells 3 and pedicle screws 2, two elements 6 made of an elastic or viscoelastic material, and two screwable plugs 7.

Figure 2:
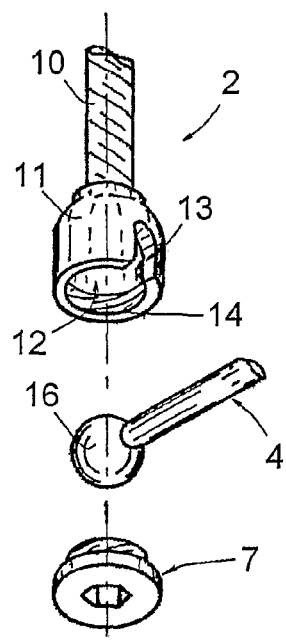
FIG. 2 is a partial view showing an exploded perspective.
Figure 3:
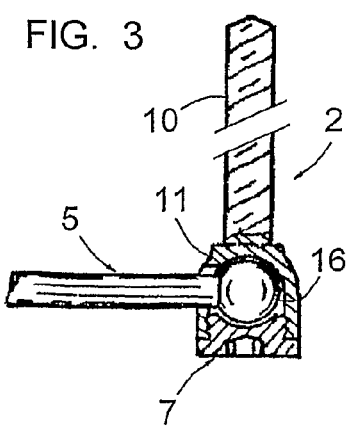
FIG. 3 is a partial sectional view after assembly.

Each pedicle screw 2 comprises a threaded bone anchor part 10 and a flared head 11. As shown in FIGS. 2 and 3, this head 11 is open at the proximal end and delimits a cavity 12 on the inside. It comprises a lateral notch 13 and has a proximal internal thread 14.

Figure 5:
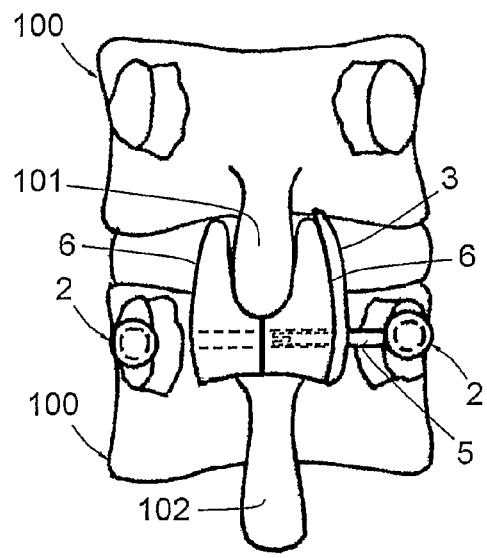
Figure 6:
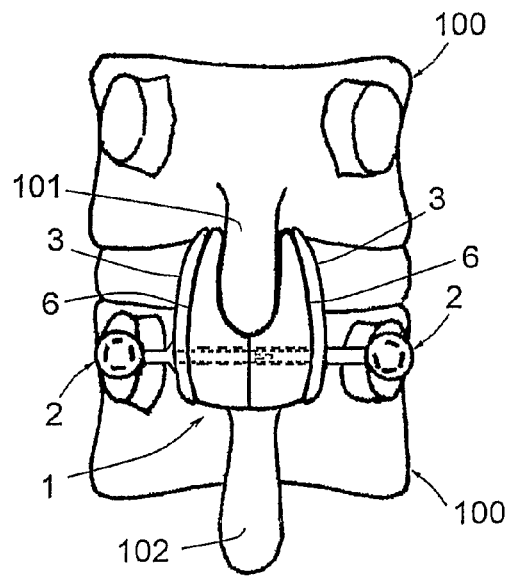
Figure 7:
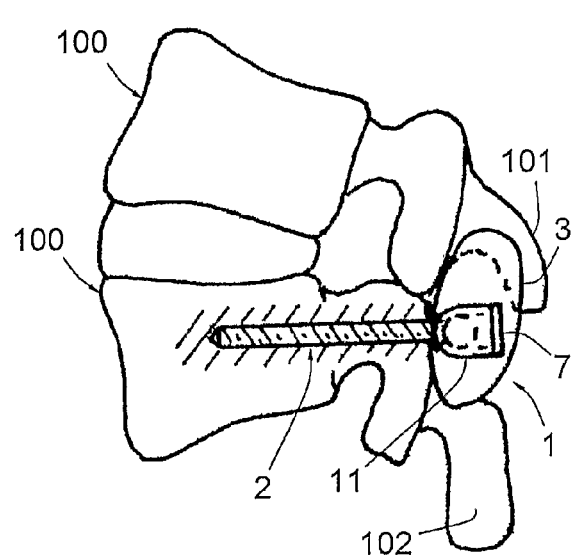
FIG. 7 is a sagittal view of the equipment after implantation.

The shells 3 are made of a rigid material, and particularly a metallic material. As shown in FIGS. 5 to 7, they will be placed on each side of the spinous process 101 of the superjacent vertebra 100, and are sized to extend over the entire height of this spinous process 101 and beyond it, towards the spinous process 102 of the vertebra 100 subjacent to it, as far as the level of the upper edge of this spinous process 102.

The shells 3 have concave parts on their sides that will face the spinous process 101 and surround the elastic elements 6, to provide longitudinal support of these elements.

One of the shells 3 is drilled with a hole 15 through which it is engaged free to slide on the connecting rod 4 that corresponds to it, while the other shell 3 is fixed to the connecting rod 5 that corresponds to it.

The connecting rod 4 may be engaged free to move in the notch 13 of the corresponding head 11 and comprises a sphere 16 that may fit free to move in the cavity 12 delimited by this head 11. The connecting rod 4 on the side opposite this sphere 16 comprises an axial threaded part 17 with a diameter less than its own diameter. In its approximately median zone, the connecting rod 4 also comprises a collar 18 acting as a stop fixing the position of the shell 3 with respect to the connecting rod.

The connecting rod 5 may be engaged in the notch 13 of the corresponding head 11, also free to move, and comprises a sphere 16 identical to that mentioned above that can also fit free to move into the cavity 12 delimited by the head 11. On the side opposite the sphere 16, the connecting rod 5 projects beyond the concave face of the shell 3 and includes an axial threaded reaming 19 opening into its free end, into which said axial threaded part 17 of the rod 4 can be fitted by screwing.

Each element 6 made of an elastic or viscoelastic material has an external convex face adapted to the concaveness of the face of the corresponding shell 3. Each element 6 comprises an upper part on its inner face forming a recess into which the spinous process 101 fits, and a lower part forming a plane face, bearing in contact with the homologous plane face of the other element 6.

Each element 6 also has a drilling 20 in it opening up at these plane faces, into which the connecting rods 4 and 5 will fit.

The threaded plugs 7 will be screwed into the proximal part of the heads 11 of the screws 2, as shown in FIG. 3.

Figure 4:
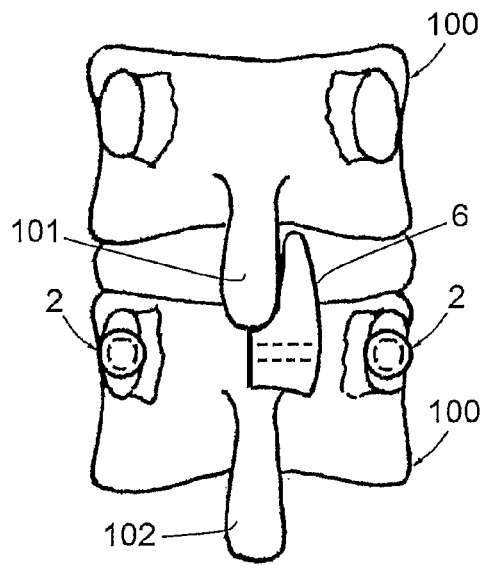
FIGS. 4 to 6 are posterior views of two vertebrae during three successive equipment implantation steps.

In practice, as can be seen in FIGS. 4 to 6, screws 2 are firstly placed in the subjacent vertebra 100 and then the element 6 in which the rod 5 will be fitted is placed in contact with the spinous process 101 (see FIG. 4). The shell 3-rod 5 assembly is then put into place with the corresponding plug 7, and the second element 6 is then put into position in contact with the spinous process 101 symmetric with the first element 6 put into place (see FIG. 5). The second shell 3 is then put into place on this second element 6 and the rod 4 is then engaged through this shell 3 and into the element 6, and is then screwed in so as to introduce its threaded part 17 into the threaded riming 19.

Screwing is continued until the sphere 16 of the rod 4 faces the corresponding head 11, and this sphere is then engaged in the cavity 12 of this head 11 before the corresponding plug 7 is put into place. As shown in FIG. 6, this screwing compresses the two elements 6, which then clamp the spinous process 101, with slight creep at the upper and lower ends of the shells 3.

After implantation, as can easily be understood, the shells 3 limit the lateral movements of the spinous process 101, and this limitation is dampened by compression of the elements 6. Due to the presence of the elements 6 between the spinous processes 101 and 102, the equipment 1 also dampens the movement of these spinous processes towards each other.

Furthermore, the equipment 1 is implanted only at the subjacent vertebra 100 and as shown in FIG. 7, the shells 3 are located at the bottom of the spinous processes 101 and 102.

Consequently, this equipment 1 is capable of keeping natural movements of the superjacent vertebra while limiting these movements so that they remain within physiological amplitudes. The equipment 1 thus replaces or assists defective natural retention elements, particularly ligaments and/or posterior joint bone masses.

Furthermore, the equipment 1 does not limit other joint movements between the two vertebrae 100 concerned, and respects the torsion axis of the vertebra which, at the lumbar level, is located at the base of the spinous processes 101, 102.

Furthermore, once the lower edges of the two elements 6 have moved towards each other, they form a fixed assembly along a globally horizontal lower line with slight concaveness at the bottom; the assembly can thus bear against the upper edge of the subjacent spinous process 102.

FIG. 8 shows equipment 1 similar to that described above, and operating in the same way.

In this case, the pedicle screws 2 are polyaxial, in other words they comprise a body 10 terminating by a sphere 25 on the proximal end, onto which an independent flared proximal head 11 is engaged, capable of multi-directional movement.

As shown in FIG. 9, each head 11 in this case comprises two diametrically opposite notches 13, and the rods 4, 5 are not provided with spheres 16.

The notches 13, rods 4, 5 and threaded plugs 7 are sized such that the plugs 7 clamp the rods 4, 5 and the spheres 25 together, thus immobilising the rods 4, 5 by sliding with respect to the heads 11 and immobilising these heads 11 with respect to the threaded bodies 10.

In this second embodiment, both of the shells 3 are fixed to the rods 4 and 5.

The rod 4 comprises a stop 18, enabling a distraction instrument 50 to bear firstly on this stop 18, and secondly against the corresponding head 11, as shown in FIG. 18. As can be seen by comparing FIGS. 10 and 11, the instrument 50 is used to slide the rod 4 with respect to the screw 2 so as to put the two elements 6 into compression, before complete tightening of the plug 7. Once this compression has been applied, the plug 7 is fully tightened so as to immobilise the rod 4 in this compression position.

The equipment 1 according to this second embodiment thus includes shells 3 not connected to each other as shown in FIG. 12.

FIG. 13 shows that the walls or shells 3 may be provided with flared areas 3a near their edges, located along the laminae of the vertebral arc 103 after implantation, conformed to match the transition zone between the spinous process 101 and these laminae.

As can be seen from the above, the invention provides equipment for surgical treatment of two vertebrae used for contention of lateral movements of the spinous process 101 of a superjacent vertebra, being implanted at a single vertebra and with contention walls 3 located at the base of said spinous process 101.

This equipment 1 can thus be used to treat two vertebrae, particularly lumbar vertebrae, both for pain and for restoration of the natural movement, particularly in the case of facet arthropathies, rotational spondylolisthesis, degeneration syndromes occurring between vertebrae located above the vertebrae affected by the arthrodesis, or recurrent post-disk arthroplasty lumbago.

Obviously, the invention is not limited to this embodiment described above as an example, but it is extended to include all forms of embodiments covered by the attached claims. In particular, the elastic elements may be made in two parts as shown, or in a single piece.

The invention claimed is:

1. Equipment for the surgical treatment of two adjacent vertebrae comprising:
    first and second bone anchors;
    a first rod assembly mounted at the first bone anchor; the first rod assembly comprising:
        a first rod section extending away from the first bone anchor along a first rod longitudinal axis; and
        a first wall disposed in spaced relation to the first bone anchor with the first rod section therebetween; the first wall extending generally normal to the first axis and having a first concave face that is concave in a direction away from the first bone anchor parallel to the first axis;
    a second rod assembly mounted at the second bone anchor; the second rod assembly comprising:
        a second rod section extending away from the second bone anchor along a second rod longitudinal axis; and
        a second wall disposed in spaced relation to the second bone anchor with the second rod section therebetween; the second wall extending generally normal to the second axis and having a second concave face that is concave in a direction away from the second bone anchor parallel to the second axis;
    wherein the first and second concave faces are disposed in spaced relation generally facing towards each other;
    a first resiliently deformable body associated with the first rod assembly and disposed both proximate the first wall and generally opposite to the first bone anchor relative to the first concave face;
    a second resiliently deformable body associated with the second rod assembly and disposed both proximate the second wall and generally opposite to the second bone anchor relative to the second concave face;
    wherein the first and second walls provide a compression force that compresses the deformable bodies toward each other between the first and second walls;
    wherein the first and second rod assemblies are configured to be arranged on each side of spinous processes of the adjacent vertebrae to limit relative pivoting movement therebetween about an axis approximately perpendicular to an invertebral disc connecting the adjacent vertebrae.

2. The equipment of claim 1 wherein the first deformable body is viscoelastic.

3. The equipment of claim 1 wherein the first and second deformable bodies jointly form a recess configured to receive a spinous process of the adjacent vertebrae.

4. The equipment of claim 1:
    wherein the first rod assembly further comprises a male threaded section;

wherein the second rod assembly further comprises a female threaded section;

wherein the male and female threaded sections are inter-engaged to couple the second rod assembly to the first rod assembly.

5. The equipment of claim 1 wherein the first and second assemblies are interconnected only through the male and female threaded sections and the first and second deformable bodies.

6. The equipment of claim 1 wherein the first and second deformable bodies abut against each other.

7. The equipment of claim 1 wherein the first and second walls include flared areas offset from the first and second rod longitudinal axes respectively.

8. The equipment of claim 1 wherein the second rod assembly further comprises a flange disposed between the second bone anchor and the second wall.

9. The equipment of claim 8 wherein the second wall is slidable relative to the flange.

10. The equipment of claim 8 wherein the flange is fixed relative to the second rod section and the second wall.

11. The equipment of claim 1 wherein the first and second bone anchors each include first and second sections that are pivotable relative to each other and lockable relative to each other in a desired angular orientation.

12. An assembly for the surgical treatment of two adjacent vertebrae comprising:

first and second bone anchors;

a first rod assembly mounted at the first bone anchor; the first rod assembly comprising:

a first rod section extending away from the first bone anchor along a first rod longitudinal axis; and a first wall disposed in spaced relation to the first bone anchor with the first rod section therebetween; the first wall extending generally normal to the first axis;

a second rod assembly mounted at the second bone anchor; the second rod assembly comprising:

a second rod section extending away from the second bone anchor along a second rod longitudinal axis; and a second wall disposed in spaced relation to the second bone anchor with the second rod section therebetween; the second wall extending generally normal to the second axis;

wherein the first and second walls are disposed in spaced relation generally facing towards each other;

a first resiliently deformable body associated with the first rod assembly and disposed both proximate the first wall and generally opposite to the first bone anchor relative to the first wall;

a second resiliently deformable body associated with the second rod assembly and disposed both proximate the second wall and generally opposite to the second bone anchor relative to the second wall;

wherein the first and second walls provide a compression force that compresses the deformable bodies against each other between the first and second walls in a direction parallel to a line extending through the first and second bone anchors;

wherein the first and second rod assemblies are configured to be arranged on each side of spinous processes of the adjacent vertebrae to limit relative pivoting movement therebetween.

* * * * *